(12) United States Patent
Morgan

(10) Patent No.: US 6,991,462 B2
(45) Date of Patent: Jan. 31, 2006

(54) DENTAL IMPLANT SYSTEM AND METHOD

(75) Inventor: Vincent J. Morgan, Boston, MA (US)

(73) Assignee: Debbie, LLC, Boston, MA (US)

( * ) Notice: Subject to any disclaimer, the term of this patent is extended or adjusted under 35 U.S.C. 154(b) by 1 day.

(21) Appl. No.: 10/662,624

(22) Filed: Sep. 15, 2003

(65) Prior Publication Data

US 2004/0063070 A1    Apr. 1, 2004

Related U.S. Application Data

(60) Provisional application No. 60/410,753, filed on Sep. 16, 2002.

(51) Int. Cl.
*A61C 8/00*    (2006.01)

(52) U.S. Cl. .................................................... 433/173

(58) Field of Classification Search ................ 433/173, 433/174, 175, 176, 201.1; D24/156
See application file for complete search history.

(56) References Cited

U.S. PATENT DOCUMENTS

| | | | | |
|---|---|---|---|---|
| RE33,796 E | * | 1/1992 | Niznick | 433/173 |
| 5,533,898 A | * | 7/1996 | Mena | 433/173 |
| 5,571,016 A | * | 11/1996 | Ingber et al. | 433/173 |
| 5,779,480 A | * | 7/1998 | Groll et al. | 433/173 |
| 6,290,500 B1 | * | 9/2001 | Morgan et al. | 433/173 |
| 6,592,370 B2 | * | 7/2003 | Morgan | 433/173 |

* cited by examiner

*Primary Examiner*—Todd E. Manahan
(74) *Attorney, Agent, or Firm*—John A. Haug

(57) ABSTRACT

An integrated abutment crown (22) has an abutment portion (24) having a central portion (24a) intermediate to a post portion (24b) receivable in the bore of an implant and a head portion which includes a nose (24c) and shelf (24d) extending from the outer circumference of the central portion to the nose. The abutment portion (24) is formed with a smooth curved surfaces for supporting crown portion (26) material applied directly onto the nose and shelf of the head portion.

9 Claims, 2 Drawing Sheets

DENTAL IMPLANT SYSTEM AND METHOD

This application claims the benefit of provisional application No. 60/410,753 filed Sep. 16, 2002.

FIELD OF THE INVENTION

This invention relates generally to restorative dentistry and more particularly to prosthesis systems and methods used with such prosthesis systems.

BACKGROUND OF THE INVENTION

The natural teeth of an individual may be lost as a result of dental disease or trauma, making it desirable to replace such teeth with one or more prosthetic devices. An example of a prosthetic device is the dental implant which is surgically positioned within the mandibular or maxillary alveolar bone.

One type of dental implant has a first implant member for placement in an osteotomy site in the alveolar bone of a patient. Following healing, a head member, commonly called an abutment, is mounted in or on the first implant member and a tooth simulating prosthesis or crown is then mounted on the abutment. A successful system of this type is disclosed in U.S. Pat. No. 4,738,623. In this patent, a first implant or root member having a first or outer end formed with a female socket circumscribed by a shoulder and having a suitable anchoring means, such as outwardly extending fins, is placed in an osteotomy site or implant receiving cavity formed in the alveolar bone with suitable surgical instruments and techniques. The first implant member is inserted into the cavity with the upper portion of the member a selected distance below the opening of the cavity, that is, below the crest of the bone, e.g., two or three millimeters. A healing plug in inserted into the female socket of the first implant member and particles of a natural and/or synthetic bone growth stimulating grafting material are then packed within the cavity around the shoulder of the implant member and the wound is then closed.

Following healing, the dentist accesses and removes the plug and replaces it with an abutment. The abutment has a male portion received within the female socket and an intermediate, outer generally hemispherical surface portion which may extend through the surface of the gingiva and preferably through the surface of the crest of the bone which may have been previously reamed to form a complimentary configuration when forming the cavity. A prosthetic device can then be attached to the abutment forming a smooth continuous surface with the hemispherical surface portion of the abutment with the interface between the prosthetic device and the abutment being supragingival or, for best aesthetics, subgingival, that is, being covered by the gingival tissue. Fabrication of the prosthetic device typically involves making an impression, generally a full arch impression, and pouring a model forming, inter alia, a positive replica, or die, of the abutment head. A laboratory technician then burnishes platinum foil over the die which serves as a core on which a prosthesis is built. Upon completion and firing of the prosthesis, the platinum is scratched away. Although this procedure has been acceptable, the efficacy of the result is dependent upon the skill of the technician and is highly labor intensive and time consuming. Alternatively, the technician could fabricate the prosthesis by a lost wax technique utilizing a central core of metal, usually a gold palladium alloy, onto which porcelain powders are added and fused in a firing oven.

In coassigned U.S. Pat. No. 6,290,500, an abutment is described and claimed in which laboratory procedures, concomitant expenses and time delays are substantially reduced. In that patent, the subject matter of which is incorporated herein by this reference, a dental implant abutment is disclosed having a central portion between a post portion and a head portion in which a circumferentially extending shelf is formed between the base of the head portion and the central portion which forms an angle with a plane perpendicular to the longitudinal axis of the head portion within a range of approximately 0–30 degrees. A prosthesis which may or may not include a sleeve core is closely fitted to the head portion and is provided with an end face at the entrance to a head receiving cavity matching the shoulder of the abutment.

In one embodiment, an integrated abutment crown is formed by providing a sleeve having an internal configuration with a negative image closely matching the outer surface of the head portion of an abutment so that the sleeve can be fitted precisely onto the head portion. The sleeve is placed on the head portion of a temporary or removable abutment having the same head portion configuration and having a post removably inserted in the bore of an implant positioned in an osteotomy site. An impression of moldable material is taken of the removable abutment and the area adjacent to the osteotomy site. The impression is removed from the patient's mouth with the sleeve remaining in the impression. A transfer abutment having a head portion with the same configuration is placed within the sleeve and the transfer abutment is inserted in an implant analog. Molding material is then poured into the impression to form a model or replica of the area adjacent to the osteotomy site with the implant analog locked in the model. The model is removed from the impression and the sleeve is removed and positioned on the transfer abutment in the model. A prosthesis is then built on a sleeve by adding suitable material and the material is shaped to fit within the available space between teeth or prosthesis contiguous to and opposing the osteotomy site. The prosthesis is then attached to a permanent abutment having a head portion with the same configuration, as by cementing or bonding, to form an integrated abutment crown. The integrated abutment crown can then be polished extraorally to remove extraneous cement when cement is used as the means of attachment and then the finished abutment can be inserted into the bore of an implant. When the post of the abutment and the bore of the implant have matching self-holding tapers, the angular position of the integrated abutment crown can be adjusted to any desired orientation and then locked in place by tapping the integrated abutment crown with a selected force. As noted in the U.S. Pat. No. 6,290,500 patent, cylindrical posts having no taper can also be used and adjusted angularly and then cemented or glued into the implant.

A special jig is provided in the patent for use with the self-holding abutment attaching system for ensuring that the locking force is imparted to the integrated abutment crown by a force which is essentially collinear with the longitudinal axis of the post portion and implant bore in a way that does not mar the surface of the crowned portion.

In a modified embodiment, a prefabricated crown element is selected for placement on the head of the removable attachment, either with or without the use of a sleeve core. A cavity is provided, or is formed, in the prefabricated crown element and adapted to receive the head portion of an abutment, or the sleeve, as described above, and the outer configuration is adapted to fit between contiguous and opposing teeth or prosthesis relative to the osteotomy site to form a finished crown. The finished crown is then attached to an abutment having a self-holding tapered post extraorally to form an integrated abutment crown for subsequent insertion into an implant having a matching self-holding tapered bore positioned within the osteotomy site. The integrated abutment crown is polished extraorally and inserted into the implant and its angular position adjusted and fixedly locked in place.

SUMMARY OF THE INVENTION

An object of the present invention is to provide an implant system and method which minimizes laboratory procedures and concomitant expenses and time delays relative to the prior art and even more efficaciously than those of U.S. Pat. No. 6,290,500 described above. Another object is the provision of apparatus and methods for producing an integrated abutment crown ready for insertion into a patient with more efficiency than in the prior art. Yet another object is the provision of an implant abutment, and method for making, which is particularly adapted to support crown material with optimum ability to bear the various forces of mastication, bruxing and light trauma experienced in usage. Still another object is the provision of such abutment crowns which allow adjustment of the angular orientation of the abutment crown at the time of mounting in the bore of an implant seated in an osteotomy site of a patient.

Briefly, in accordance with the invention, integrated abutment crowns are formed by taking an abutment portion having a central portion disposed between a post portion receivable in the bore of an implant and a head portion for supporting the material of the crown. For purposes of the following description and as seen in the accompanying drawings, the head portion will be referred to and shown as being above the post portion, however it will be realized that the actual orientation in use will vary in dependence on the osteotomy site. A shelf is formed extending from the outer periphery of the central portion to a nose extending upwardly from the central portion. Although the shelf can form any angle relative to the longitudinal axis of the head portion, it is preferred that the shelf slope upwardly from the outer periphery of the central portion toward the nose at an angle of approximately between 10 and 40 degrees with the axis. The outer periphery of the shelf may be at a single height around the outer circumference of the central portion relative to the free end of the nose or it may be varied to adjust to anatomical features, such as following the gingival contour of the patient. The shelf forms a smooth curved surface with the nose to provide enhanced force bearing member. The nose is formed with a rounded free end and may be generally conical or any other suitable shape that supports the material of the crown. Although various attachment mechanisms with an implant can be employed, the preferred mechanism is a self-holding or locking taper that allows adjustable angular orientation for placement in an implant.

In accordance with the invention, the surface of the head portion is sand blasted to enhance bonding to crown material applied thereto. The crown material is selected to be chromatically and aesthetically similar to adjacent dentition and to have the capability of bearing the various forces of mastication, bruxing and light trauma associated with usage. Such materials include ceramics and porcelains, polymers, polyceramic resins, glass ionomers and other composite materials. In a preferred method, the crown is built on the head portion of the abutment portion by applying layers of a polyceramic material and light curing the material.

According to the invention, methods of application and curing of the selected crown material include those which can be processed by heating to temperatures that are not injurious to the material of the crown or abutment while still assuring sufficient bonding to the head portion.

Additional objects and features of the invention will be set forth in part in the description which follows and in part will be obvious from the description. The objects and advantages of the invention may be realized and attained by means of the instrumentalities, combinations and methods particularly pointed out in the appended claims.

BRIEF DESCRIPTION OF THE DRAWINGS

The accompanying drawings, which are incorporated in and constitute a part of the specification, illustrate preferred embodiments of the invention and, together with the description, serve to explain the objects, advantages and principles of the invention. In the drawings.

DETAILED DESCRIPTION OF THE PREFERRED EMBODIMENTS

Figure 1:
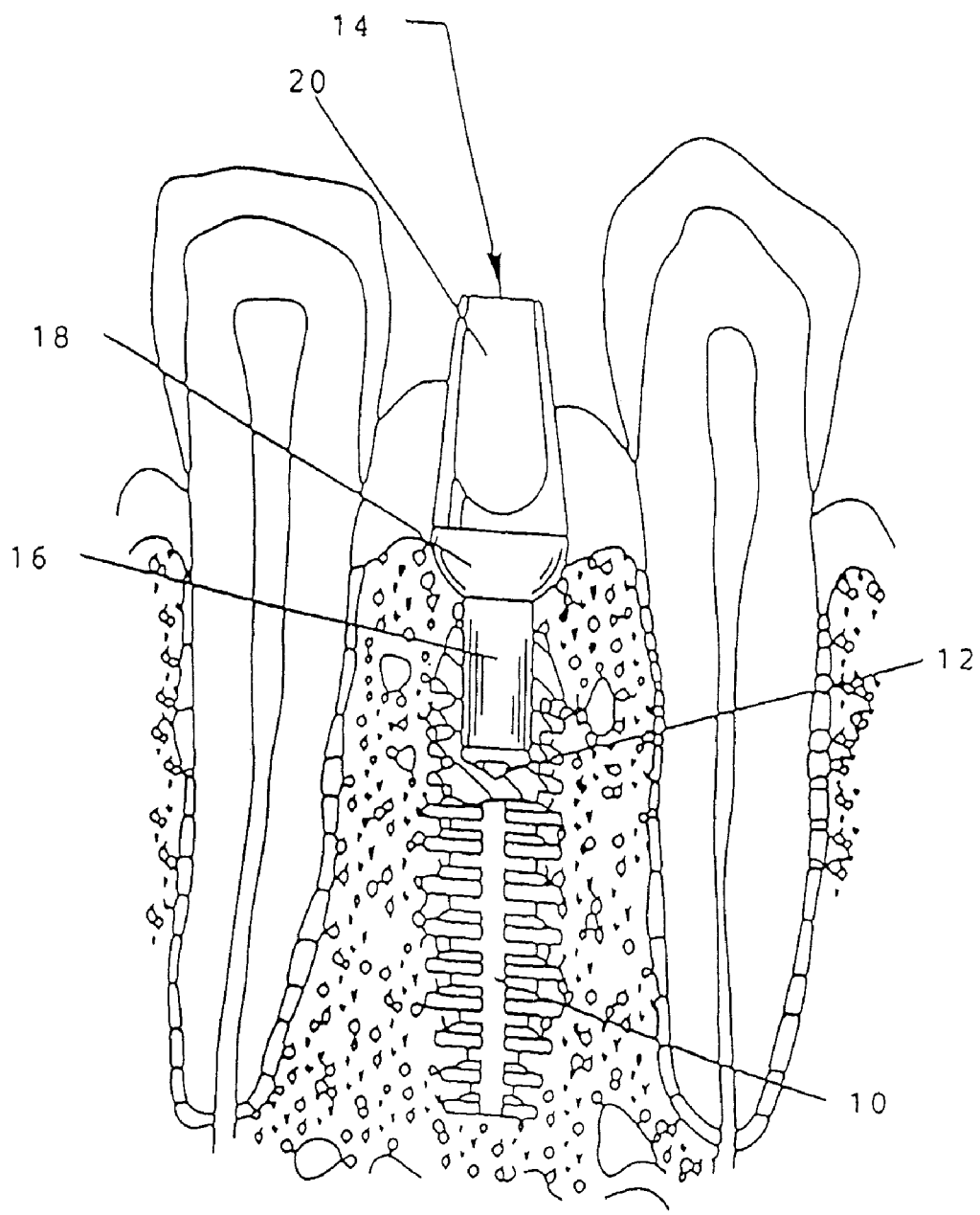
FIG. 1 is a broken away cross sectional elevational view of a jaw showing an abutment positioned in an implant in an osteotomy site along with contiguous dentition in accordance with the teaching of U.S. Pat. No. 4,738,623.

FIG. 1 shows a prior art system comprising an implant 10 disposed in an osteotomy site in the jaw of a patient. Implant 10 has a bore 12 formed with a self-holding taper and mounts therein an abutment 14 having a post portion 16 formed with a matching self-holding taper so that the abutment can be locked in place by tapping the abutment along the longitudinal axis of the post portion with at least a selected force. Abutment 14 has a central portion or base 18 formed with a smooth curved outer surface configuration and a head portion 20 which serves to mount a prosthesis thereon. Further details can be obtained by reference to U.S. Pat. No. 4,738,623, referenced above, the subject matter of which is incorporated herein by this reference.

In accordance with the prior art, a crown or other prosthesis is typically fabricated by a relatively labor intensive and time consuming process involving the burnishing of platinum foil on the head of an abutment which is then built upon and shaped to fit within the space available between contiguous teeth, as shown in FIG. 1, or prosthesis, and opposing teeth or prosthesis (not shown). After completion of the prosthesis, the foil has to be removed, as by scraping, before the prosthesis can be permanently attached to the abutment mounted in the implant. If cement is used in attaching to the abutment, care must be taken to avoid having extraneous cement on the outer surface which would irritate the gingiva.

As noted above, according to the teaching of U.S. Pat. No. 6,290,500, fabrication of a prosthesis is simplified by first forming the crown utilizing an abutment analog. The abutment analog and the permanent abutment are formed with an identical shelf extending between the upstanding part of the head portion and the crown. The crown, with or without a sleeve core, is separately fabricated on the analog abutment and formed with an end face having a configuration selected to match the configuration of the shoulder, e.g., having the same slope angle. The crown is then received on and cemented to the abutment thereby integrating the crown and abutment so that the prosthesis can be finished and polished extraorally. This facilitates the subgingival placement of the cement interface since there will be no flash or excess cement to irritate the gingival tissue. The finished integrated abutment crown, preferably having a post portion with a self-holding taper, is then inserted into the implant, its angular orientation adjusted as desired and finally tapped into locking engagement in the implant as a single unit utilizing a customized seating device.

In accordance with a preferred embodiment of the present invention, cement margins between the crown and the abutment portion are entirely eliminated, as will be discussed below.

Figure 2:
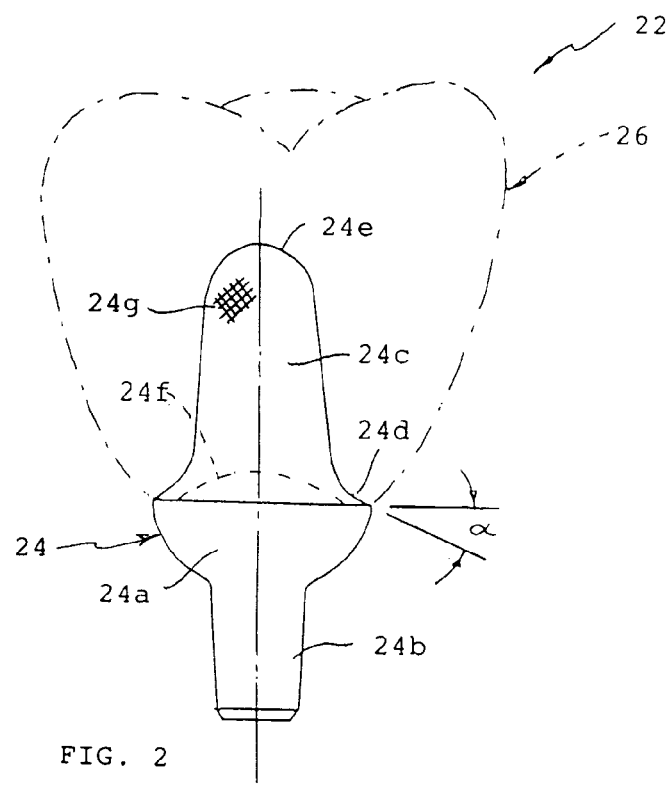
FIG. 2 is an elevational view of an abutment portion of an integrated abutment crown of the invention shown with the crown material indicated in dashed lines.

With respect to FIG. 2, an integrated abutment crown 22 made in accordance with the invention is shown having an abutment portion 24 and a crown portion 26 indicated in dashed lines.

Abutment portion 24 is formed of suitable biocompatible material such as titanium or titanium alloy and has a central portion 24a having a smooth curved surface which typically is circular in a horizontal cross section (as shown in the drawing) but can be of other configurations, such as elliptical. In the following discussion it will be considered as circular for the example given. Central portion 24a has a downwardly (with reference to the orientation shown in the drawing) extending post portion 24b for receipt in the bore of an implant such as shown in FIG. 1. Although various attachment mechanisms can be employed for attaching the abutment portion to the implant, a generally cylindrical post having a self-holding taper matching a self-holding taper of a bore of the implant, as in the above referenced patents, is preferred.

A nose 24c extends upwardly from central portion 24a and a shelf 24d extends from the maximum circumferential portion of the central portion to nose 24c and is joined to the nose by a smooth curved surface. The nose is generally conical but can be of any suitable configuration for supporting the crown material and has a free end 24e formed with a smooth curved surface. The curved smooth surface facilitates the incremental chemical and mechanical addition of various prosthetic materials to be discussed and to minimize stress concentration. The outer portion of the shelf may be at a single height about its circumference, i.e., the distance from the extremity of the free portion of the nose being constant about its periphery, or it may be varied, as indicated by dashed line 24f, to adjust to anatomical features, such as following the gingival contour. The angle that the outer circumferential portion of the shelf makes with a plane perpendicular to the longitudinal axis of nose 24c can be of any selected degree, however it is preferred that the shelf slope upwardly toward the nose at an angle of between approximately 10 to 40 degrees with the said plane.

Crown portion 26 is applied directly to the surface of the head portion comprising nose 24c and shelf 24d.

Figure 3:
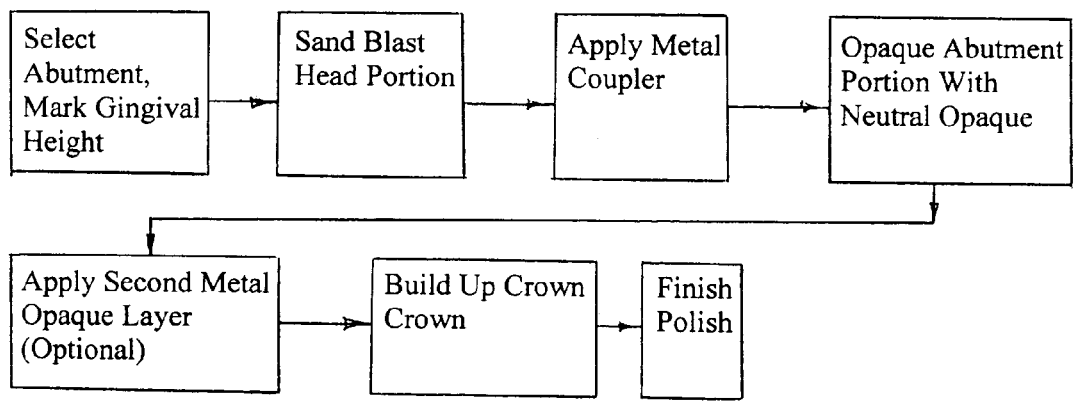
FIG. 3 is a schematic view showing steps of a preferred method for applying crown material to the abutment portion.

With reference to FIG. 3, in accordance with one preferred method for fabricating the integrated abutment crown using polyceramic materials available from one of various available sources, such as DRM Research Laboratories, Inc. of Branford, Conn., (hereinafter referred to as DRM), a suitable non-shouldered abutment portion is selected and tried in an analog implant in a model of the osteotomy site which includes at least adjacent and opposite dentition. Implant analogs such as those shown in copending, coassigned application Ser. No. 10/093,991, filed Mar. 7, 2002, which issued as U.S. Pat. No. 6,688,887 on Feb. 10, 2004, the subject matter of which is incorporated herein by this reference, can be used. The gingival height is marked and shoulder 24d is formed, or a suitable abutment portion having a preformed shoulder is selected. The head portion of the abutment portion is preferably rouhgened to enhance retention of prosthetic material applied thereto by being air blasted with suitable media, such as 50 micron alumina oxide as indicated by broken away portion 24g of FIG. 2, and then cleaned with 95 percent ethyl alcohol in an ultrasonic bath for approximately five minutes. The abutment portion is air dried with an oil free compressed air source or, if not available, by using a hair dryer.

Two drops of a metal coupler (#C313 of DRM) are stirred and applied to the head portion in four to six thin coats with a suitable instrument such as a brush. Air is blown on each of the coats to remove excess liquid and the coats gently dried. A slightly cloudy or milky appearance indicates sufficient coverage. After thorough air drying, the abutment portion is baked in an oven for five minutes at approximately 120 degrees C. with no vacuum.

The abutment portion is then opaqued with a neutral metal opaque powder (#C421 of DRM). This step is required for certain shades and is optional for other shades.

Approximately two drops of metal opaque liquid (#C318 of DRM) and one heaping spatular tip of neutral metal opaque powder (#C421 of DRM) is taken with the powder incorporated into the liquid in three incremental steps, and spatulated to form a smooth creamy mix. A single coat is applied and the abutment portion then baked at approximately 120 degrees C. for five minutes preferably with a vacuum to increase bond strength. A ceramo coupler (#B204 of DRM) is applied and gently air dried. Ceramo coupler is required between two opaque layers. The abutment portion is bench cooled for one minute and a thin coat of modeling liquid (#C312 of DRM) is applied if a second layer of metal opaque is not going to be applied.

A second metal opaque layer of appropriate shade may be applied. As in the first opaque layer application, two drops of opaque liquid is incorporated into one heaping spatular tip of neutral opaque powder in three incremental steps and spatulated to form a smooth creamy mix. A single coat is applied with a brush. While the degree of mixing is not critical, the coat should be applied quickly. The abutment portion is then oven baked at approximately 120 degrees C. for five minutes with vacuum; again vacuum is not essential but does increase bond strength. The abutment portion is then bench cooled for one minute and then ceramo coupler applied and gently air dried. Modeling liquid (#C312 of DRM) is applied and light cured for two minutes.

The crown is then built up in four applications of a) opaque dentin—40 percent up to 70 percent of total crown;
b) dentin—40 percent down to 10 percent of total crown;
c) enamel—15 percent of total crown; and
d) incisal—5 percent of total crown.

The specific identity of the opaque dentin, dentin and enamel vary with the particular shade chosen. By way of example, the following applications will be described for vita shade A3. The incisal chosen for this example is incisal clear.

In application a) a flat strip of opaque dentin (A3—#C338 of DRM) is patted out on a glass slab; the opaque dentin is applied to the surface extending to the cervical margins all around the abutment portion while avoiding air inclusions; this application is repeated for 40 to 70 percent of the crown thickness; the result is light cured for four minutes.

In application b) a flat strip of dentin (A3—#C328 of DRM) is patted out on a glass slab; the dentin is applied directly onto the opaque layer and anatomical features are placed; intrinsic stains are incorporated as required; the result is light cured for two minutes.

In application c) a flat strip of enamel (A3—#C377 of DRM) is patted out on a glass slab; the enamel is applied directly to the dentin layer; the morphology is shaped and contacts and margins applied; when the intrinsic characterization is completed, the enamel is light cured for two minutes.

In application d) the incisal (Clear—#311 of DRM) is applied directly onto the enamel and characterized by using different opacities; the morphology is shaped and occlusion is adjusted; after stain pits, fissures etc., the incisal is light cured for two minutes.

Finishing is performed using a superior grade diamond fine cut carbide bur for obtaining a final unpolished crown. Polishing is then performed using silicone discs to remove oxide layers and cuts, a nylon bristle brush for smoothing the surface and a buff wheel used with paste.

It is within the purview of the invention to apply at least the opaque layer to the head portion for receipt of prosthetic material in the form of a prefabricated prosthetic blank at least partially contoured which can be made in a quality controlled environment for later attachment to the opaqued head portion, as by light curing and subsequent polishing.

Although the above materials are known in the dental prosthesis industry, they have not been applied directly onto an abutment portion but rather have been used, to fabricate a crown portion, for example on a sleeve core as in U.S. Pat. No. 6,290,500, discussed above, which is in turn connected to an abutment.

Repairs to existing integrated abutment crowns can be made intraorally by reducing existing material as necessary, then cleaning with 95 percent ethyl alcohol and air drying, applying ceramo coupler and drying and then applying modeling liquid, light curing for one minute and adding appropriate material, as described above. Such repairs can result from a need to add a contact point, alter the crown contour, correct the color of the post having undergone a color change, join adjacent units and repair fractures or seating divets.

As alluded to in the last paragraph with reference to repairing seating divets, angulated integrated abutment crowns made in accordance with the invention can be notched to provide a directional seating platform. Subsequently the resulting divot can be re-contoured after seating of the prosthesis.

As noted above, various materials can be used for fabricating the crown by directly bonding or attaching the material by chemical or mechanical means without the use of cement, for example, ceramics and porcelains, polymers, polyceramic resins, glass ionomers and other composite materials which are capable of being chromatically and aesthetically similar to adjacent dentition as well as having the ability of withstanding the various forces of mastication, bruxing and light trauma and can be cured by means which are not injurious to the material of the crown or the abutment while having sufficient bonding to the abutment portion. It will be realized that the specific steps of application would be adjusted for the particular materials selected, as required.

The invention also provides the ability to add prosthetic material only to a portion of the head portion of the abutment portion since a sleeve is not required, as well as to add prosthetic material below the height of contour of the abutment portion which is not possible with sleeve type systems.

The invention provides a method for providing an integrated abutment crown in which materials in various forms can be used in providing different characterizations as well as an abutment portion that has dimensions consistent with clinical realities.

The invention has been described with regard to specific preferred embodiments thereof, however, variations and modifications will become apparent to those skilled in the art. For example, suitable prosthetic material, partially or completely prefabricated in a quality controlled manner, could be attached to the abutment portion to facilitate the efficiency and accuracy of fabrication of the prosthesis. As noted above, the abutments also can be preformed with a shelf, if desired. For example, several standard variations could be provided to fit different requirements. This approach would allow making the abutment in a more easily controlled high quality environment and to make it convenient and more expeditious for the addition of the crown material. It is therefore the intention that the appended claims be interpreted as broadly as possible in view of the prior art to include all such variations and modification.

What is claimed is:

1. An abutment for use with an implant having a first end and a second end and a longitudinal axis passing through the first end, the implant having a bore formed through the first end and extending along the longitudinal axis, the abutment comprising a central portion between a post portion and a head portion, the post portion having a longitudinal axis and being receivable in the bore of the implant, the central portion formed with a smoothly curved outer surface extending from a relatively large diameter progressively down to a smaller diameter where the central portion joins the post portion, the head portion having a longitudinal axis and having a nose extending along the longitudinal axis to a rounded free end, a shelf being formed between the central portion and the nose, the shelf having an outer portion and an inner portion, the outer portion forming a selected angle with a plane generally perpendicular to the longitudinal axis of the head portion and the inner portion forming a smooth curved surface with the nose, the shelf and nose forming a smooth continuous surface extending from the central portion and adapted to support crown material received thereon.

2. An abutment according to claim 1 in which the central portion has a circumference and the distance between the free end of the nose and the outer part of the shelf is essentially constant around the circumference of the central portion.

3. An abutment according to claim 1 in which the central portion has a circumference and the distance between the free end of the nose and the outer part of the shelf varies around the circumference of the central portion in conformity with a selected gingival contour.

4. An abutment according to claim 1 in which the longitudinal axes of the head portion and the post portion are essentially collinear when the post portion is received in the bore of the implant.

5. An abutment according to claim 1 in which the bore of the implant is formed with a self-holding taper and the post portion of the abutment is formed with a matching self-holding taper for receipt in the bore of the implant.

6. An abutment according to claim 1 in which the post portion is cylindrical without a taper and is attachable to an implant by an attachment media.

7. An abutment according to claim 1 in which the head portion is formed with a roughened surface for enhanced retention of prosthetic material applied directly to the abutment surface.

8. An abutment according to claim 1 further comprising prosthetic material including an opaque layer applied to the head portion and further including a tooth shaped prosthetic piece shaped to fit on the head portion for later attachment thereto and being adapted for final contouring and polishing to fit a specific clinical application.

9. An abutment according to claim 1 further comprising a crown formed of a plurality of layers of prosthetic material applied to the head portion.

* * * * *